(12) United States Patent
Muratore et al.

(10) Patent No.: US 9,085,516 B2
(45) Date of Patent: Jul. 21, 2015

(54) COMPOUNDS WITH A WOODY NOTE

(75) Inventors: Agnés Muratore, Valbonne (FR); Jean-Jacques Chanot, Speracedes (FR)

(73) Assignee: V. MANE FILS, Bar sur Loup (FR)

( * ) Notice: Subject to any disclaimer, the term of this patent is extended or adjusted under 35 U.S.C. 154(b) by 99 days.

(21) Appl. No.: 13/696,177

(22) PCT Filed: May 4, 2011

(86) PCT No.: PCT/IB2011/051976
§ 371 (c)(1),
(2), (4) Date: Jan. 28, 2013

(87) PCT Pub. No.: WO2011/138747
PCT Pub. Date: Nov. 10, 2011

(65) Prior Publication Data
US 2013/0123548 A1     May 16, 2013

(30) Foreign Application Priority Data

May 5, 2010   (FR) ..................................... 10 01938

(51) Int. Cl.
| | | |
|---|---|---|
| C07C 35/08 | (2006.01) | |
| C07C 35/18 | (2006.01) | |
| A61K 8/34 | (2006.01) | |
| A61Q 13/00 | (2006.01) | |
| A61Q 19/10 | (2006.01) | |
| C07C 31/135 | (2006.01) | |
| C07C 33/14 | (2006.01) | |
| C07C 403/08 | (2006.01) | |
| C11B 9/00 | (2006.01) | |
| C07C 35/17 | (2006.01) | |

(52) U.S. Cl.
CPC . *C07C 35/18* (2013.01); *A61K 8/34* (2013.01); *A61Q 13/00* (2013.01); *A61Q 19/10* (2013.01); *C07C 31/1355* (2013.01); *C07C 33/14* (2013.01); *C07C 35/08* (2013.01); *C07C 35/17* (2013.01); *C07C 403/08* (2013.01); *C11B 9/0034* (2013.01); *C07C 2101/14* (2013.01); *C07C 2101/16* (2013.01)

(58) Field of Classification Search
CPC ................................. C07C 35/18; C07C 35/17
USPC .......................................................... 512/22
See application file for complete search history.

(56) References Cited

U.S. PATENT DOCUMENTS

| | | | |
|---|---|---|---|
| 4,000,329 A | 12/1976 | Pittet et al. | |
| 4,081,481 A | 3/1978 | Sprecker et al. | |
| 4,147,672 A | 4/1979 | Schulte-Elte et al. | |
| 4,229,600 A | 10/1980 | Kobayashi et al. | |
| 4,264,467 A | 4/1981 | Schulte-Elte et al. | |
| 4,289,659 A | 9/1981 | Schulte-Elte et al. | |
| 4,387,048 A | 6/1983 | Yoshida | |
| 4,524,017 A | 6/1985 | Inoue et al. | |
| 4,585,594 A | 4/1986 | Himmele et al. | |
| 5,114,915 A | 5/1992 | Fehr et al. | |
| 5,234,902 A * | 8/1993 | Levorse, Jr. ..................... | 512/22 |
| 6,489,273 B1 | 12/2002 | Aida et al. | |
| 6,943,272 B2 | 9/2005 | Mane et al. | |
| 7,064,102 B2 | 6/2006 | Eh | |
| 7,563,925 B1 | 7/2009 | Levorse | |
| 7,683,023 B2 | 3/2010 | Gaudin | |
| 7,704,933 B2 | 4/2010 | Moretti et al. | |
| 2003/0148919 A1 | 8/2003 | Markert et al. | |
| 2005/0182273 A1* | 8/2005 | Eh .................................. | 560/259 |
| 2008/0039360 A1 | 2/2008 | Kraft | |

FOREIGN PATENT DOCUMENTS

| | | |
|---|---|---|
| DE | 1643710 | 6/1971 |
| DE | 3023483 | 10/1987 |
| FR | 2 008 167 | 1/1970 |
| JP | S60-152437 | 8/1985 |

OTHER PUBLICATIONS

International Search Report for PCT/IB2011/051975 dated Aug. 16, 2011.
International Preliminary Report on Patentability for PCT/IB2011/051975 dated Nov. 6, 2012.
Frackowiak et al: "Stereochemistry of terpene derivatives. Part 4: Fragrant terpenoid derivatives with an unsaturated gem-dimethylbicyclo[3.1.0]hexane system", Tetrahedron Asymmetry, Pergamon Press Ltd, Oxford, GB, vol. 16, No. 20, (Oct. 17, 2005), pp. 3352-3360.
Hashidoko Y et al: "Bisabolane sesquiterpenes and a 2-phenoxychromone from *Rosa woodsii* leaves", Phytochemistry, Pergamon Press, GB, vol. 31, No. 6, (Jun. 1, 1992), pp. 2148-2149.
Chilean Office Action dated May 11, 2012 regarding Chile Application No. 3080-2012.
Chinese Office Action dated Jan. 10, 2014 regarding Chinese Application No. 201180022496.7.
Japanese Office Action dated Jan. 6, 2015 regarding Japanese Application No. 2013-508607.
Wang, et al., "Analysis of fragrance compositions of precious coniferous woods grown in Taiwan", 2006, pp. 528-532, vol. 60, Holzfoschung.
Kraft, Y, et al. "Synthesis and Odor of Aliphatic Musks: Discovery of a New Class of Odorants" European Journal of Organic Chemistry, vol. 2004, Issue 2, Jan. 2004, pp. 354-365.

* cited by examiner

*Primary Examiner* — Ling Choi
*Assistant Examiner* — Lanee Reuther
(74) *Attorney, Agent, or Firm* — B. Aaron Schulman, Esq.; Stites & Harbison, PLLC.

(57) ABSTRACT

The invention relates to the chemistry of fragrances and to the field of perfumery. It relates more particularly to compounds with a woody note, responding to the general formula:

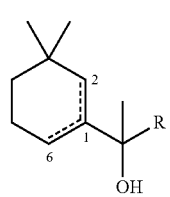

in which:
the ring with 6 carbon atoms is saturated or has a double bond between carbons C1 and C2 or between carbons C1 and C6,
R is selected from a $C_2$-$C_5$ alkyl or $C_2$-$C_5$ alkenyl group.

12 Claims, No Drawings

COMPOUNDS WITH A WOODY NOTE

The invention relates to the chemistry of fragrances and to the field of perfumery. It relates more particularly to a novel family of compounds with a woody note, and extends to the use of these compounds in perfumery.

In order to increase the range of notes offered to perfumers for their creations, the perfumery industry is constantly searching for novel fragrant compounds.

Today there are many compounds with a woody note. As examples, we can cite, in particular:
- derivatives of norbornane or of norbornene, such as those described in U.S. Pat. No. 4,229,600, U.S. Pat. No. 4,524,017, WO 2003/035595, or
- derivatives of decalone, described in particular in WO 2007/031904, U.S. Pat. No. 4,387,048 and U.S. Pat. No. 5,114,915.

We can also cite FR 2 259 091 which, by means of a particular general formula, designates a family of compounds claimed as being distinguished by "their fruity and at once woody, green and oily note". In this family are included in particular the following ketones:
1-(3,3-dimethyl-cyclohexyl)-pent-4-en-1-one;
1-(3,3-dimethyl-cyclohex-1-enyl)-pent-4-en-1-one;
1-(3,3-dimethyl-cyclohex-6-enyl)-pent-4-en-1-one;
1-(3,3-dimethyl-cyclohex-1-enyl)-hex-4-en-1-one;
1-(3,3-dimethyl-cyclohex-6-enyl)-hex-4-en-1-one;
1-(3,3-dimethyl-cyclohex-6-enyl)-2-methyl-but-3-en-1-one.

In apparently fortuitous manner, this document (diagram VII) also describes the synthesis of particular secondary alcohols such as 1-(3,3-dimethylcyclohex-1-enyl)-pent-4-enol and 1-(3,3-dimethylcyclohex-6-enyl)-pent-4-enol, which nevertheless do not correspond to the general formula mentioned above of the compounds having a "fruity and at once woody, green and oily note". This document is moreover silent as to the fragrance which they release. After verification, the inventors have not found a woody note, but a low-intensity, rather green, fruity fragrance of pineapple.

In spite of a significant number of compounds already existing with a woody note, there remains a need for novel nuances in the woody fragrances. Beyond this first objective, the invention also aims to propose compounds, which are easily accessible due to simple manufacture compatible with the requirements of the industry, and which, through considerable stability, can be used in perfumery, in a wide range of applications.

The term "perfumery" is here used in its general sense; it designates not only traditional perfumery (alcoholic or otherwise), but also the other fields in which the fragrance of products is important. Reference can thus be made to perfumery compositions in the usual and traditional sense (such as perfuming bases and concentrates, perfumes, eaux de Cologne, eaux de toilette, air-fresheners, room odorisers, perfumed candles and similar products), to topical compositions (in particular cosmetics, such as face and/or body creams, talcum powders, hair oils, shampoos, hair lotions, bath salts and oils, shower and/or bath gels, toilet soaps, antiperspirants and body deodorants, shaving lotions and creams, soaps, dentifrices, mouthwashes, ointments, and similar products), as well as to cleaning products, in particular household (such as detergents, laundry detergents, softeners, air-fresheners, room odorisers and similar products).

The invention thus has as its object compounds of general formula below:

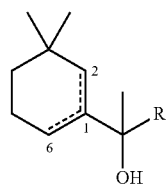

I in which:
  the ring with 6 carbon atoms is saturated or has a double bond between carbons C1 and C2 or between carbons C1 and C6,
  R is selected from a $C_2$-$C_5$ alkyl or $C_2$-$C_5$ alkenyl group.

The compounds corresponding to this formula (I) all release more or less subtle or pronounced woody notes, enriched with more or less floral, fruity, green and/or animal notes.

Also, they have the advantage of being obtainable in a relatively simple manner, from easily accessible primary materials, i.e. dehydrolinalool (DE 1643710) or some of its particular derivatives, such as dehydroherbac (U.S. Pat. No. 4,264,467) and herbac. Diagram 1 below summarises the essential steps thereof.

Diagram 1

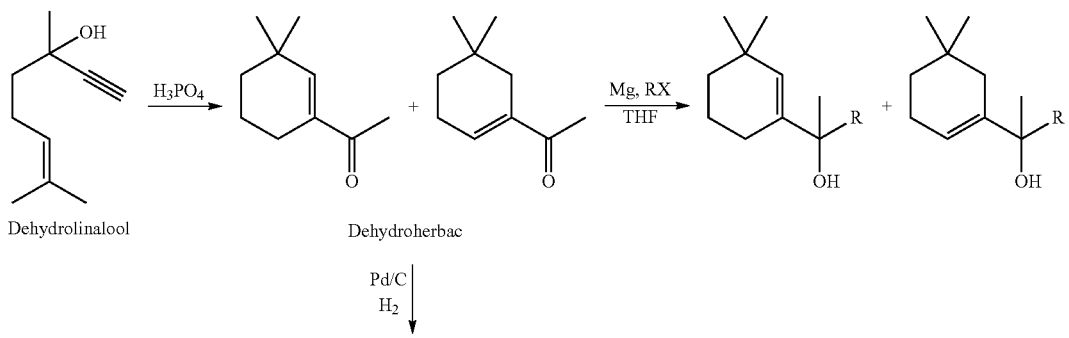

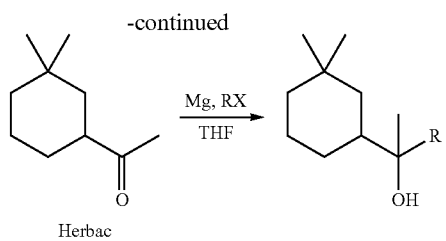

Herbac (R is as defined above, and X refers to a starting group, such as a halogen atom -preferably bromine-)

In conventional manner, the name "dehydroherbac" designates a mixture of the isomers 1-(3,3-dimethylcyclohex-1-enyl)ethanone and 1-(3,3-dimethylcyclohex-6-enyl)ethanone; the relative proportion of these isomers is unimportant.

Pure forms of these isomers can be obtained from dehydroherbac, using well-known separation methods, such as separation by crystallisation and/or by chromatography. They can also be obtained selectively by synthesis, as is described in particular in Z. Chem. (1969): 9, 64 and in U.S. Pat. No. 4,264,467.

Like dehydroherbac, 1-(3,3-dimethylcyclohex-1-enyl)ethanone and 1-(3,3-dimethylcycloyhex-6-enyl)ethanone, in their pure form, can be used as starting products for the preparation of the compounds of formula (I) of the invention.

Within the meaning of the present invention, the term "$C_2$-$C_5$ alkyl" designates any monovalent radical derived from a saturated, linear or branched carbon chain, containing 2 to 5 carbon atoms, in particular the ethyl, n-propyl, i-propyl, n-butyl, i-butyl, t-butyl and pentyl, 1(or 2)-methylpropyl, 1,2-dimethylpropyl, 1,1-dimethylpropyl, 1(or 2 or 3)-methylbutyl . . . groups.

Similarly, the term "$C_2$-$C_5$ alkenyl" designates any monovalent radical derived from a linear or branched carbon chain containing 2 to 5 carbon atoms and having a double bond, in particular the ethenyl, prop-1-enyl, prop-2-enyl, but-1-enyl, but-2-enyl, but-3-enyl, pent-1-enyl, pent-2-enyl, pent-3-enyl, pent-4-enyl, 2-methylprop-2-enyl, 2,3-dimethylprop-1-enyl, 3-methylbut-3-enyl . . . groups. Alkenyls containing 3 to 5 carbon atoms ($C_3$-$C_5$ alkenyls) are nevertheless preferred, in particular the prop-2-enyl, but-3-enyl, but-2-enyl, pent-4-enyl, pent-3-enyl and pent-2-enyl groups.

In a first embodiment, the invention relates to compounds of formula (I), as defined above, and for which the ring with 6 carbon atoms is saturated.

According to a second embodiment, the invention relates to compounds of formula (I), as defined above, and for which the ring with 6 carbon atoms has a double bond between carbons C1 and C2 or between carbons C1 and C6.

In both cases, advantageously and according to the invention, R is selected from the groups: —$CH_2CH_3$, —$CH_2CH_2$=$CH_2$, —$CH_2CH_2CH_3$, —$CH_2CH_2CH_2CH_3$, —$CH_2CH(CH_3)_2$, —$CH(CH_3)CH_2CH_3$ and —$CH_2CH_2CH(CH_3)_2$.

In particular, the preferred compounds of the invention are selected from:
2-(3,3-dimethylcyclohex-1-enyl)butan-2-ol
2-(5,5-dimethylcyclohex-1-enyl)butan-2-ol
2-(3,3-dimethylcyclohex-1-enyl)pent-4-en-2-ol
2-(5,5-dimethylcyclohex-1-enyl)pent-4-en-2-ol
2-(3,3-dimethylcyclohex-1-enyl)pentan-2-ol
2-(5,5-dimethylcyclohex-1-enyl)pentan-2-ol
2-(3,3-dimethylcyclohex-1-enyl)hexan-2-ol
2-(5,5-dimethylcyclohex-1-enyl)hexan-2-ol
2-(3,3-dimethylcyclohex-1-enyl)-4-methylpentan-2-ol
2-(5,5-dimethylcyclohex-1-enyl)-4-methylpentan-2-ol
2-(3,3-dimethylcyclohex-1-enyl)-3-methylpentan-2-ol
2-(5,5-dimethylcyclohex-1-enyl)-3-methylpentan-2-ol
2-(3,3-dimethylcyclohex-1-enyl)-5-methylhexan-2-ol
2-(5,5-dimethylcyclohex-1-enyl)-5-methylhexan-2-ol
2-(3,3-dimethylcyclohexyl)butan-2-ol
2-(3,3-dimethylcyclohexyl)pent-4-en-2-ol
2-(3,3-dimethylcyclohexyl)pentan-2-ol
2-(3,3-dimethylcyclohexyl)hexan-2-ol
2-(3,3-dimethylcyclohexyl)-4-methylpentan-2-ol
2-(3,3-dimethylcyclohexyl)-5-methylhexan-2-ol Due to the pleasant fragrance which they release, the compounds of the invention find numerous applications in perfumery, in particular for the preparation of traditional perfumes, of cosmetic compositions and of cleaning products.

The invention also relates to the use of the compounds of the invention for the preparation of a fragrancing composition or of a fragrancing article in the applications described above and/or below, in particular in perfumery, in cosmetics, and for the preparation of cleaning products, particularly domestic cleaning products.

The invention thus extends to perfumed compositions comprising at least one compound of the invention. It can in particular concern traditional perfumery compositions, cosmetic compositions, cleaning products, or "so-called intermediate compositions", intended to be used for the preparation of compositions or finished products (in particular perfumes, cosmetic products, cleaning products).

Such perfumed compositions are generally prepared from a base product, in which the compound or compounds of the invention are to be incorporated. The base product will easily be determined by the man skilled in the art depending on the composition envisaged and therefore on the use envisaged. The composition of these base products and the nature of their usual components, such as solvent(s) and/or adjuvant(s), are well known to the man skilled in the art.

The compounds entering into these perfumed compositions, in particular the compounds of the invention, can be incorporated in or on an inert support material. The support materials which can be used are many and various, for example polar solvents, oils, greases, finely divided solids, cyclodextrins, maltodextrins, gums, resins and any other known support material for such compositions (for example, soaps, candles, ointments, textiles, wipes, perfumed gels . . . ).

The effective quantity of the compounds of the invention to be incorporated in these compositions is dependent on the nature of said compositions, on the required fragrancing effect and on the nature of the other fragrancing compounds possibly present. It is easily determined by the man skilled in the art, and can vary within a very extended range, from 0.1 to 99%, in particular 0.1 to 50%, particularly 0.1 to 30%. The preceding percentages are expressed by total weight of the composition.

The invention relates in particular to a traditional perfume composition (in particular a perfuming base or concentrate, an eau de Cologne, an eau de toilette, a perfume . . . ) comprising at least one compound of the invention or a composition (for example, a so-called intermediate composition) itself comprising at least one compound of the invention.

The invention also relates in particular to a cosmetic composition (particularly, face and/or body cream, talcum powder, oil for hair or for the body, shampoo, hair lotion, bath salts, bath oil, shower gel, bath gel, soap, antiperspirant, deodorant, lotion, shaving cream, shaving soap, toothpaste, ointment . . . ) comprising at least one compound of the invention or a composition (for example, a so-called intermediate composition) itself comprising at least one compound of the invention.

The invention also relates to a cleaning product (in particular, softener, detergent, laundry detergent, air-freshener, room odoriser . . . ) comprising at least one compound of the invention or at least one composition (for example, a so-called intermediate composition) itself comprising at least one compound of the invention.

The presence of centres of asymmetry in the structure of the compounds of formula (I) according to the invention causes the existence, for each of them, of a plurality of enantiomeric and/or diastereomeric forms. The invention also covers the compounds represented by general formula (I) in the form of mixtures of enantiomers and/or diastereomers, in variable proportions, in particular the racemic mixtures. The invention also comprises the compounds of formula (I) in the form of a single enantiomer and/or diastereomer. Mixtures of enantiomers/diastereomers or pure forms can be obtained by synthesis from optically enriched or optically pure starting products, or by means of methods of separation by crystallisation or chromatography.

The following examples illustrate a particular manner of preparing the compounds of the invention, as well as the olfactive profile of each of the compounds exemplified. These examples are only given for the purpose of illustration and must not be understood as limiting the general scope of the invention.

EXAMPLE 1

Preparation of 2-(3,3-dimethylcyclohex-1-enyl)butan-2-ol and 2-(5,5-dimethylcyclohex-1-enyl)butan-2-ol 1.2 eq. of magnesium covered with THF are placed under nitrogen in a three-necked flask. 1.2 eq. of bromoethane are run in drop by drop. The temperature is raised to reflux. When the magnesium is entirely consumed, the reaction medium is placed at 5-10° C. and 1 eq. of dehydroherbac is running drop by drop. The mixture is then agitated at ambient temperature for two hours, and then poured onto an HCl 10% aq./ice mixture (50:50). After about ten minutes of agitation, the phases are separated. The aqueous phase is extracted twice with MTBE (methyl and tert-butyl ether). The reunited organic phases are washed with a solution of sodium bicarbonate and then with salt water.

After drying on magnesium sulphate, filtration on paper and evaporation of the solvent, a raw product is obtained composed of two isomers in an alpha/beta proportion of 90:10, when the starting dehydroherbac is an alpha/beta mixture of 85:15. A raw product is obtained composed of two isomers in an alpha/beta proportion of 60:40, when the starting dehydroherbac is an alpha/beta mixture of 60:40.

In both cases, the raw product is distilled under reduced pressure.

BP=60° C./0.4 torr

Olfactive description 90:10: woody, pine, eucalyptus, very powerful.

Olfactive description 60:40: woody, camphorated, very powerful.

Alpha Isomer:
$^1$H-NMR (200 MHz, CDCl$_3$): δ (ppm) 0.76 (t, 3H), 0.97 (s, 6H), 0.82-1.13 (m, 3H), 1.25 (s, 3H), 1.35-1.41 (m, 2H), 1.50-1.61 (m, 3H), 1.85-1.91 (m, 2H), 5.41 (s, 1H).
$^{13}$C-NMR (50 MHz, CDCl3): δ (ppm) 8.2, 20.2, 27.2, 30.2, 30.3, 32.9, 37.5, 48.8, 54.3, 75.1, 130.5, 139.4.
MS [e/m (%)]: 182 (M+, 0.3), 154 (11), 153 (100), 109(16), 95(13), 81 (71), 57 (18), 55 (10), 43 (48), 41 (10).

Beta Isomer:
$^1$H-NMR (200 MHz, CDCl$_3$): δ (ppm) 0.76 (t, 3H), 0.97 (s, 6H), 0.82-1.13 (m, 3H), 1.25 (s, 3H), 1.35-1.41 (m, 2H), 1.50-1.61 (m, 3H), 1.85-1.91 (m, 2H), 5.56-5.68 (m, 1H).
$^{13}$C-NMR (50 MHz, CDCl$_3$): δ (ppm) 9.2, 12.3, 26.1, 29.2, 30.4, 32.1, 33.3, 41.3, 42.6, 53.7, 122.4, 128.3.
MS [e/m (%)]: 182 (M+, 5), 167 (10), 154 (25), 153 (33), 138 (34), 126 (25), 125 (29), 113 (20), 112 (10), 11 (12), 110 (57), 109 (16), 98 (11), 97 (40), 95 (19), 83 (100), 70 (16), 69 (73), 67 (14), 57 (22), 56 (33), 55 (75), 53 (13), 43 (18), 42 (12), 41 (51), 39 (18).

If desired, techniques well-known to the man skilled in the art, such as fractional distillation, can allow separation of these two isomers: 2-(3,3-dimethylcyclohex-1-enyl)butan-2-ol and 2-(5,5-dimethylcyclohex-1-enyl)butan-2-ol (respectively designated alpha and beta isomers, hereabove). For example, a distillation using a column with a metallic lining permits isolation in a first stage of the alpha isomer: under 1 torr, it distils at 55° C. at the top of the column. Then, if the distillation is continued, after a few fractions of alpha-beta mixture, the beta isomer can be isolated: under 1 torr, it distils at 58° C. at the top of the column.

Similarly, these isomers can be obtained selectively, by synthesis; replacing, in the preceding protocol, the hydroherbac with 1-(3,3-dimethylcyclohex-1-enyl)ethanone or 1-(3,3-dimethylcyclohex-6-enyl)ethanone.

EXAMPLE 2

Preparation of 2-(3,3-dimethylcyclohex-1-enyl)pent-4-en-2-ol and 2-(5,5-dimethylcyclohex-1-enyl)pent-4-en-2-ol The protocol of example 1 is carried out again with allyl chloride replacing bromoethane.

The raw product formed, composed of two isomers in an alpha/beta proportion of 88:12, is distilled under reduced pressure.

BP=55° C./0.2 torr

Olfactive description: woody, animal, medium power.

Alpha Isomer:
$^1$H-NMR (200 MHz, CDCl$_3$): δ (ppm) 0.97 (s, 6H), 1.26 (s, 3H), 1.30-1.41 (m, 2H), 1.59-1.65 (m, 2H), 1.75 (d, J=2.2 Hz, 1H), 1.92 (td, J=1.2 and 6.0 Hz, 2H), 2.16-2.45 (m, 2H), 5.04-5.13 (m, 2H), 5.42 (s, 1H), 5.61-5.79 (m, 1H).
$^{13}$C-NMR (50 MHz, CDCl$_3$): δ (ppm) 20.15, 25.07, 27.17, 30.33, 31.57, 37.09, 45.12, 73.92, 118.42, 130.68, 134.08, 139.56.
MS [e/m (%)]: 194 (M+, 0), 154 (11), 153 (100), 109 (21), 95 (12), 91 (10), 81 (94), 67 (12), 43 (79), 41 (17).

Beta Isomer:
$^1$H-NMR (200 MHz, CDCl$_3$): δ (ppm) 0.91 (s, 6H), 1.26 (s, 3H), 1.30-1.41 (m, 2H), 1.59-1.65 (m, 2H), 1.75 (d, J=2.2 Hz, 1H), 1.92 (td, J=1.2 and 6.0 Hz, 2H), 2.16-2.45 (m, 2H), 5.04-5.13 (m, 2H), 5.42 (s, 1H), 5.61-5.79 (m, 1H).
$^{13}$C-NMR (50 MHz, CDCl3): δ (ppm) 23.00, 23.79, 28.12, 32.17, 34.88, 40.31, 50.19, 73.92, 118.64, 128.56, 134.08, 139.56.
MS [e/m (%)]: 194 (M+, 0), 154 (10), 153 (100), 97 (34), 95 (40), 79 (12), 69 (14), 67 (11), 59 (10), 55 (13), 43 (20), 41 (23), 39 (11).

If desired, 2-(3,3-dimethylcyclohex-1-enyl)pent-4-en-2-ol and 2-(5,5-dimethylcyclohex-1-enyl)pent-4-en-2-ol thus obtained can be separated, for example, by fractional distillation. Similarly, they can be obtained selectively, by synthesis, from 1-(3,3-dimethylcyclohex-1-enyl)ethanone and 1-(3,3-dimethylcyclohex-6-enyl)ethanone.

EXAMPLE 3

Preparation of 2-(3,3-dimethylcyclohex-1-enyl)pentan-2-ol and 2-(5,5-dimethylcyclohex-1-enyl)pentan-2-ol The protocol of example 1 is carried out again with 1-bromopropane replacing bromoethane.
The raw product obtained, composed of two isomers in an alpha/beta proportion of 95:5, is distilled under reduced pressure.

BP=53° C./0.2 torr

Olfactive description: woody, animal, rustic, powerful.
Alpha Isomer:
$^1$H-NMR (200 MHz, CDCl3): δ (ppm) 0.85-1.07 (m, 6H), 0.97 (s, 6H), 1.25 (s, 3H), 1.35-1.50 (m, 4H), 1.54-1.70 (m, 4H), 1.88 (td, J=1.2 and 6.0 Hz, 2H), 2.07-2.28 (m, 2H), 5.40 (s, 1H).
$^{13}$C-NMR (50 MHz, CDCl$_3$): δ (ppm) 14.54, 17.21, 20.20, 24.98, 27.64, 30.25, 30.37, 31.58, 37.13, 42.88, 74.94, 130.19, 139.96.
MS [e/m (%)]: 196 (M+, 0.3), 154 (10), 153 (100), 109 (15), 95 (12), 91 (11), 81 (67), 71 (14), 43 (47), 41 (12).
Beta Isomer:
MS [e/m (%)]: 196 (M+, 0.8), 154 (15), 153 (100), 97 (24), 95 (34), 69 (10), 43 (17), 41 (14).

If desired, 2-(3,3-dimethylcyclohex-1-enyl)pentan-2-ol and 2-(5,5-dimethylcyclohex-1-enyl)pentan-2-ol thus obtained can be separated, for example, by fractional distillation. Similarly, they can be obtained selectively, by synthesis, from 1-(3,3-dimethylcyclohex-1-enyl)ethanone and 1-(3,3-dimethylcyclohex-6-enyl)ethanone.

EXAMPLE 4

Preparation of 2-(3,3-dimethylcyclohex-1-enyl)hexan-2-ol and 2-(5,5-dimethylcyclohex-1-enyl)hexan-2-ol The protocol of example 1 is carried out again with 1-bromobutane replacing bromoethane.
The raw product obtained is composed of two isomers in an alpha/beta proportion of 92:8 when the starting dehydroherbac is an alpha/beta mixture of 85:15, and 80:20, when the starting dehydroherbac is an alpha/beta mixture of 60:40.

BP=57° C./0.2 torr

Olfactive description 92:8: woody, animal, slightly fresh, everlasting facet, medium power.
Olfactive description 80:20: woody, minty, raspberry facet, powerful.
Alpha Isomer:
$^1$H-NMR (200 MHz, CDCl$_3$): δ (ppm) 0.85-1.07 (m, 6H), 0.97 (s, 6H), 1.26 (s, 3H), 1.37-1.31 (m, 1H), 1.35-1.43 (m, 3H), 1.48-1.52 (m, 2H), 1.59-1.67 (m, 2H), 1.88 (td, J=1.2 and 6.0 Hz, 2H), 2.08-2.28 (m, 2H), 5.40 (s, 1H).
$^{13}$C-NMR (50 MHz, CDCl$_3$): δ (ppm) 14.11, 20.21, 23.09, 24.97, 26.11, 27.65, 30.25, 30.37, 31.58, 37.14, 40.16, 74.91, 130.24, 139.94.
MS [e/m (%)]: 210 (M+, 0.3), 154 (11), 153 (100), 109 (12), 81 (57), 43 (32).
Beta Isomer:
MS [e/m (%)]: 210 (M+, 0.7), 153 (100), 97 (20), 95 (28), 43 (11), 41 (10).

If desired, 2-(3,3-dimethylcyclohex-1-enyl)hexan-2-ol and 2-(5,5-dimethylcyclohex-1-enyl)hexan-2-ol thus obtained can be separated, for example, by fractional distillation. Similarly, they can be obtained selectively, by synthesis, from 1-(3,3-dimethylcyclohex-1-enyl)ethanone and 1-(3,3-dimethylcyclohex-6-enyl)ethanone.

EXAMPLE 5

Preparation of 2-(3,3-dimethylcyclohex-1-enyl)-4-methylpentan-2-ol and 2-(5,5-dimethylcyclohex-1-enyl)-4-methylpentan-2-ol The protocol of example 1 is carried out again with 1-bromo-2-methylpropane replacing bromoethane.
The raw product obtained, composed of two isomers in an alpha/beta proportion of 95:5, is distilled under reduced pressure.

BP=48° C./0.2 torr

Olfactive description: woody, fresh, minty, powerful.
Alpha Isomer:
$^1$H-NMR (200 MHz, CDCl$_3$): δ (ppm) 0.88 (d, J=7.4 Hz, 3H), 0.92 (d, J=7.4 Hz, 3H), 0.97 (s, 6H), 1.03-1.07 (m, 1H), 1.26 (s, 3H), 1.35-1.49 (m, 5H), 1.54-1.68 (m, 3H), 1.89 (td, J=1.4 and 5.8 Hz, 2H), 5.44 (s, 1H).
$^{13}$C-NMR (50 MHz, CDCl$_3$): δ (ppm) 20.09, 24.32, 24.40, 25.25, 28.78, 29.90, 30.40, 31.52, 37.03, 48.88, 75.36, 129.91, 140.13.
MS [e/m (%)]: 210 (M+, 0, 1), 154 (12), 153 (100), 109 (15), 81 (59), 57 (10), 43 (37), 41 (11).
Beta Isomer:
MS [e/m (%)]: 210 (M+, 0.6), 154 (14), 153 (100), 97 (28), 95 (33), 69 (11), 57 (10), 43 (16), 41 (16).

If desired, 2-(3,3-dimethylcyclohex-1-enyl)-4-methylpentan-2-ol and 2-(5,5-dimethylcyclohex-1-enyl)-4-methylpentan-2-ol thus obtained can be separated, for example, by fractional distillation. Similarly, they can be obtained selectively, by synthesis, from 1-(3,3-dimethylcyclohex-1-enyl)ethanone and 1-(3,3-dimethylcyclohex-6-enyl)ethanone.

EXAMPLE 6

Preparation of 2-(3,3-dimethylcyclohex-1-enyl)-3-methylpentan-2-ol and 2-(5,5-dimethylcyclohex-1-enyl)-3-methylpentan-2-ol The protocol of example 1 is carried out again with 2-bromobutane replacing bromoethane.

The raw product obtained, composed of four isomers (two alpha diastereomers and beta diastereomers) in the proportion 47:40:7:6, is distilled under reduced pressure.

Olfactive description: woody, fatty, chlorinated, insecticide, medium power.

BP=48° C./0.2 torr

4 Superimposed Isomers:
$^1$H-NMR (200 MHz, CDCl$_3$): δ (ppm) 0.82-0.93 (m, 6H), 0.97 (s, 3H), 1.19 and 1.21 (2s, 3H), 1.40-1.71 (m, 7H), 1.88 (m, 2H).
$^{13}$C-NMR (50 MHz, CDCl$_3$, 47%): δ (ppm) 12.94, 13.20, 20.23, 23.51, 23.94, 24.85, 30.29, 31.64, 37.18, 41.44, 72.18, 130.63, 140.52.
$^{13}$C-NMR (50 MHz, CDCl$_3$, 40%): δ (ppm) 12.85, 12.99, 20.23, 23.77, 23.79, 24.89, 30.20, 30.39, 31.64, 31.18, 41.30, 72.18, 130.63, 140.52.
MS [e/m (%)], 47% isomer: 210 (M+, 0, 1), 154 (11), 153 (100), 109 (18), 95 (10), 81 (78), 43 (45), 41 (12).
MS [e/m (%)], 40% isomer: 210 (M+, 0, 2), 154 (10), 153 (100), 109 (20), 95 (11), 81 (80), 43 (46), 41 (12).
MS [e/m (%)], 7% isomer: 210 (M+, 0), 154 (11), 153 (100), 97 (30), 95 (38), 69 (11), 43 (14), 41 (16).
MS [e/m (%)], 6% isomer: 210 (M+, 0), 154 (11), 153 (100), 97 (25), 95 (27), 43 (13), 41 (13).

If desired, 2-(3,3-dimethylcyclohex-1-enyl)-3-methylpentan-2-ol and 2-(5,5-dimethylcyclohex-1-enyl)-3-methylpentan-2-ol thus obtained can be separated, for example, by fractional distillation. Similarly, they can be obtained selectively, by synthesis, from 1-(3,3-dimethylcyclohex-1-enyl)ethanone and 1-(3,3-dimethylcyclohex-6-enyl)ethanone.

EXAMPLE 7

Preparation of 2-(3,3-dimethylcyclohex-1-enyl)-5-methylhexan-2-ol and 2-(5,5-dimethylcyclohex-1-enyl)-5-methylhexan-2-ol The protocol of example 1 is carried out again with 3-methyl-1-bromobutane replacing bromoethane.

The raw product obtained, composed of two isomers in an alpha/beta proportion of 89:11, is distilled under reduced pressure.

BP=85° C./0.4 torr

Olfactive description: woody, dry hay, honey, powerful.
Alpha Isomer:
$^1$H-NMR (200 MHz, CDCl$_3$): δ (ppm) 0.87 (d, J=6.4 Hz, 6H), 0.97 (s, 6H), 1.02-1.09 (m, 2H), 1.26 (s, 3H), 1.35-1.62 (m, 8H), 1.88 (td, J=1.0 and 5.8 Hz, 2H), 5.40 (s, 1H).
$^{13}$C-NMR (50 MHz, CDCl$_3$): δ (ppm) 20.19, 22.63, 22.70, 24.95, 27.70, 28.33, 30.26, 30.35, 31.59, 32.92, 37.13, 38.11, 74.92, 130.34, 139.83.
MS [e/m (%)]: 224 (M+, 0.2), 154 (11), 153 (100), 135 (10), 109 (13), 81 (64), 43 (42), 41 (11).
Beta Isomer:
$^1$H-NMR (200 MHz, CDCl$_3$): δ (ppm) 0.87 (d, J=6.4 Hz, 6H), 0.97 (s, 6H), 1.02-1.09 (m, 2H), 1.26 (s, 3H), 1.35-1.62 (m, 8H), 1.88 (td, J=1.0 and 5.8 Hz, 2H), 5.60-0.66 (m, 1H).
MS [e/m (%)]: 224 (M+, 0); 154 (17), 153 (100), 97 (26), 95 (30), 69 (12), 43 (23), 41 (11).

If desired, 2-(3,3-dimethylcyclohex-1-enyl)-5-methylhexan-2-ol and 2-(5,5-dimethylcyclohex-1-enyl)-5-methylhexan-2-ol thus obtained can be separated, for example, by fractional distillation. Similarly, they can be obtained selectively, by synthesis, from 1-(3,3-dimethylcyclohex-1-enyl)ethanone and 1-(3,3-dimethylcyclohex-6-enyl)ethanone.

EXAMPLE 8

Preparation of 2-(3,3-dimethylcyclohexyl)butan-2-ol

The protocol of example 1 is carried out again with herbac replacing dehydroherbac.

The raw product obtained, composed of three isomers in a proportion of 38:37:25, is distilled at reduced pressure.

BP=59° C./1.0 torr

Olfactive description: woody, fruity, linalool, powerful.
3 Superimposed Isomers:
$^1$H-NMR (200 MHz, CDCl$_3$): δ (ppm) 0.85-0.93 (m, 12H), 1.03-1.13 (m, 4H), 1.32-1.59 (m, 8H).
$^{13}$C-NMR (50 MHz, CDCl$_3$, majority isomers (38 and 37%)): δ (ppm) 7.53 and 7.77, 22.56 and 23.23, 23.41 and 23.58, 24.66 and 24.74, 26.54 and 27.10, 32.28 and 32.39, 33.78, 34.59 and 35.66, 39.17 and 39.23, 41.66 and 41.80, 74.37 and 74.44.
MS [e/m (%)], 38% isomer: 224 (M+, 0), 155 (12), 95 (11), 73 (100), 72 (16), 69 (14), 55 (19), 43 (15), 41 (11).
MS [e/m (%)], 37% isomer: 224 (M+, 0), 155 (13), 137 (10), 95 (12), 73 (100), 72 (17), 69 (15), 55 (20), 43 (15), 41 (12).
MS [e/m (%)], 25% isomer: 224 (M+, 0), 155 (36), 137 (31), 113 (100), 111 (15), 99 (50), 95 (17), 86 (18), 85 (10), 83 (12), 81 (14), 73 (11), 71 (10), 69 (24), 57 (34), 56 (15), 55 (29), 43 (28), 41 (25).

EXAMPLE 9

Preparation of 2-(3,3-dimethylcyclohexyl)pent-4-en-2-ol

The protocol of example 1 is carried out again with allyl chloride replacing bromoethane, and herbac replacing dehydroherbac.

The raw product obtained, composed of three isomers in a proportion of 42:41:17, is distilled under reduced pressure.

BP=72° C./0.4 torr

Olfactive description: woody, floral, green, powerful.
3 Superimposed Isomers:
$^1$H-NMR (200 MHz, CDCl$_3$): δ (ppm) 0.88-0.93 (3s, 6H), 0.82-1.00 (m, 2H), 1.08-1.09 (3s, 3H), 1.32-1.64 (m, 7H), 2.12-2.32 (m, 2H), 5.06-5.17 (m, 2H), 5.78-5.95 (m, 1H).
$^{13}$C-NMR (50 MHz, CDCl$_3$, majority isomers (42 and 41%)): δ (ppm) 22.50, 23.50 and 23.86, 24.64 and 24.71, 26.57 and 27.23, 30.84 and 30.94, 33.75, 39.18 and 39.24, 39.71 and 40.66, 42.51 and 42.55, 44.36 and 44.43, 73.77 and 73.89, 118.59 and 118.66, 134.03 and 134.16.
MS [e/m (%)], 42% isomer: 196 (M+, 0), 156 (11), 155 (100), 137 (65), 111 (53), 95 (51), 85 (46), 84 (17), 81 (38), 69 (59), 67 (13), 55 (31), 45 (13), 43 (98), 41 (35), 39 (11).
MS [e/m (%)], 41% isomer: 196 (M+, 0), 156 (12), 155 (97), 137 (61), 111 (52), 97 (10), 95 (51), 85 (45), 84 (18), 81 (37), 69 (60), 67 (15), 55 (32), 45 (12), 43 (100), 41 (33), 39 (13).
MS [e/m (%)], 17% isomer: 196 (M+, 0, 7), 156 (10), 155 (100), 138 (10), 137 (80), 125 (27), 111 (40), 98 (16), 97 (22), 95 (45), 85 (14), 84 (12), 83 (97), 81 (39), 69 (80), 59 (21), 57 (23), 56 (21), 55 (65), 53 (12), 43 (56), 42 (12), 41 (65), 39 (20).

EXAMPLE 10

Preparation of 2-(3,3-dimethylcyclohexyl)pentan-2-ol

The protocol of example 1 is carried out again with 1-bromopropane replacing bromoethane and herbac replacing dehydroherbac.

The raw product obtained, composed of three isomers in a proportion of 79:19:2, is distilled under reduced pressure.

BP=60° C./0.2 torr

Olfactive description: woody, fresh, linalool, sweet, powerful.

3 Superimposed Isomers:
$^1$H-NMR (200 MHz, CDCl$_3$): δ (ppm) 0.89-0.92 (2s and 1t superimposed, 9H), 1.03-1.09 (m, 2H), 1.07-1.09 (2s, 3H), 1.31-1.83 (m, 11H).
$^{13}$C-NMR (50 MHz, CDCl$_3$, 79% isomers): δ (ppm) 14.77, 16.64, 22.53, 24.12, 24.67, 27.14, 30.85, 33.78, 39.24, 39.76, 42.41, 42.48, 74.44.
$^{13}$C-NMR (50 MHz, CDCl$_3$, 19% isomers): δ (ppm) 16.44, 16.68, 22.56, 23.89, 24.74, 26.60, 30.92, 33.78, 39.18, 40.59, 42.30, 42.34, 74.33.
MS [e/m (%)], 79% isomer: 198 (M+, 0), 155 (16), 137 (11), 95 (11), 87 (100), 86 (12), 69 (18), 55 (11), 45 (21), 43 (15), 41 (13).
MS [e/m (%)], 19% isomer: 198 (M+, 0), 155 (16), 137 (10), 95 (10), 87 (100), 86 (11), 69 (19), 55 (10), 45 (20), 43 (15), 41 (12).
MS [e/m (%)], 2% isomer: 198 (M+, 0), 155 (38), 137 (32), 127 (100), 113 (48), 111 (14), 100 (12), 95 (14), 83 (13), 81 (13), 71 (24), 69 (24), 57 (16), 56 (12), 55 (26), 43 (34), 41 (25).

EXAMPLE 11

Preparation of 2-(3,3-dimethylcyclohexyl)hexan-2-ol

The protocol of example 1 is carried out again with 1-bromobutane replacing bromoethane and herbac replacing dehydroherbac.

The raw product obtained, composed of three isomers in a proportion of 77:21:2, is distilled under reduced pressure.

BP=68° C./0.2 torr

Olfactive description: woody, animal, medium power.

3 Superimposed Isomers:
$^1$H-NMR (200 MHz, CDCl$_3$): δ (ppm) 0.89-0.92 (2s and it superimposed, 9H), 1.03-1.09 (m, 2H), 1.08-1.09 (2s, 3H), 1.31-1.83 (m, 13H).
$^{13}$C-NMR (50 MHz, CDCl$_3$, 77% isomers): δ (ppm) 14.17, 16.64, 22.39, 24.15, 24.68, 25.60, 27.15, 30.93, 33.78, 39.18, 39.68, 39.79, 42.34, 74.30.
$^{13}$C-NMR (50 MHz, CDCl$_3$, 21% isomers): δ (ppm) 16.69, 22.57, 23.95, 24.76, 25.47, 26.58, 30.85, 33.78, 39.23, 39.75, 40.57, 42.23, 74.40.
MS [e/m (%)], 77% isomer: 212 (M+, 0), 155 (20), 137 (11), 101 (100), 95 (10), 69 (13), 55 (14), 45 (10), 43 (12), 41 (11).
MS [e/m (%)], 21% isomer: 212 (M+, 2), 155 (48), 141 (100), 137 (33), 127 (41), 111 (13), 95 (15), 85 (16), 83 (11), 81 (13), 71 (12), 69 (20), 57 (19), 55 (23), 43 (20), 41 (23).
MS [e/m (%)], 2% isomer: 212 (M+, 1), 156 (11), 155 (57), 141 (44), 137 (32), 127 (21), 111 (11), 101 (100), 100 (13), 95 (23), 83 (10), 81 (20), 71 (15), 69 (17), 55 (37), 53 (10), 45 (12), 43 (28), 41 (21).

EXAMPLE 12

Preparation of 2-(3,3-dimethylcyclohexyl)-4-methylpentan-2-ol

The protocol of example 1 is carried out again with 1-bromo-2-methylpropane replacing bromoethane, and herbac replacing dehydroherbac.

The raw product is obtained, composed of three isomers in a proportion of 85:14:1, is distilled under reduced pressure.

BP=58° C./0.2 torr

Olfactive description: woody, fresh, slightly citronella and banana, medium power.
$^1$H-NMR (200 MHz, CDCl$_3$): δ (ppm) 0.81-1.06 (m, 2H), 0.89-0.98 (2s and 2d superimposed, 12H), 1.09-1.10 (2s, 3H), 1.34-1.85 (m, 10H).
$^{13}$C-NMR (50 MHz, CDCl$_3$, 85% isomers): δ (ppm) 22.54, 23.73, 24.22, 24.74, 24.89, 25.02, 26.73, 30.96, 33.77, 39.28, 40.72, 43.47, 48.24, 75.09.
$^{13}$C-NMR (50 MHz, CDCl$_3$, 14% isomers): δ (ppm) 23.64, 23.82, 24.37, 24.82, 25.09, 27.37, 30.89, 33.80, 39.23, 39.88, 43.51, 48.24, 74.98.
MS [e/m (%)], 85% isomer: 212 (M+, 0), 155 (26), 137 (13), 101 (100), 95 (11), 69 (15), 59 (14), 57 (21), 55 (11), 43 (19), 41 (15).
MS [e/m (%)], 14% isomer: 212 (M+, 2), 155 (40), 141 (100), 137 (28), 127 (33), 111 (14), 95 (15), 85 (22), 83 (12), 81 (16), 71 (11), 69 (23), 57 (22), 56 (11), 55 (24), 43 (25), 41 (28).
MS [e/m (%)], 1% isomer: 212 (M+, 0), 155 (46), 137 (24), 111 (10), 101 (100), 95 (23), 85 (11), 83 (10), 81 (12), 69 (14), 59 (13), 58 (11), 57 (22), 45 (10), 43 (26), 41 (19).

EXAMPLE 13

Preparation of 2-(3,3-dimethylcyclohexyl)-3-methylpentan-2-ol

The protocol of example 1 is carried out again with 2-bromobutane replacing bromoethane, and herbac replacing dehydroherbac.

The raw product obtained, composed of five isomers in a proportion of 26:25:24:20:5, is distilled under reduced pressure.

BP=64° C./0.2 torr

Olfactive description: woody, artemisia, delicious, subtle.

5 Superimposed Isomers:
$^1$H-NMR (200 MHz, CDCl$_3$): δ (ppm) 0.80-1.05 (m, 4H), 0.89-0.95 (m, 12H), 0.99-1.01 (s superimposed, 3H), 1.31-1.82 (m, 9H).
MS [e/m (%)], 26% isomer: 212 (M+, 0, 2), 155 (48), 141 (11), 137 (33), 111 (21), 101 (100), 95 (24), 81 (15), 72 (10), 69 (26), 59 (14), 57 (20), 55 (21), 45 (21), 43 (26), 41 (22).
MS [e/m (%)], 25% isomer: 212 (M+, 0, 1), 155 (42), 137 (26), 111 (20), 101 (100), 95 (19), 81 (13), 69 (23), 59 (13), 57 (15), 55 (16), 45 (19), 43 (19), 41 (17).
MS [e/m (%)], 24% isomer: 212 (M+, 0), 155 (36), 137 (26), 111 (16), 101 (100), 95 (18), 81 (11), 69 (60), 59 (11), 57 (15), 55 (15), 45 (20), 43 (17), 41 (16).

MS [e/m (%)], 20% isomer: 212 (M+, 0), 155 (40), 137 (25), 111 (21), 101 (100), 95 (21), 81 (13), 69 (22), 59 (11), 57 (15), 55 (16), 45 (19), 43 (19), 41 (18).

MS [e/m (%)], 5% isomer: 212 (M+, 1), 155 (57), 141 (100), 137 (59), 127 (12), 111 (20), 97 (20), 95 (27), 85 (15), 83 (24), 81 (19), 71 (18), 69 (36), 67 (14), 59 (15), 57 (39), 56 (13), 55 (39), 43 (41), 41 (33).

EXAMPLE 14

Preparation of 2-(3,3-dimethylcyclohexyl)-5-methylhexan-2-ol

The protocol of example 1 is carried out again with 3-methyl-1-bromobutane replacing bromoethane, and herbac replacing dehydroherbac.

The raw product obtained, composed of three isomers in a proportion of 46:43:11, is distilled under reduced pressure.

BP=71° C./0.4 torr

Olfactive description: woody, pine, fresh, clean, powerful.
3 Superimposed Isomers:

$^1$H-NMR (200 MHz, CDCl$_3$): δ (ppm) 0.88-0.94 (s superimposed, 12H), 0.87-1.00 (m, 2H), 1.04-1.12 (m, 1H), 1.07-1.08 (2s, 3H), 1.17-1.26 (m, 3H), 1.31-1.32 (m, 1H), 1.39-1.53 (m, 7H), 1.57-1.83 (m, 1H).

$^{13}$C-NMR (50 MHz, CDCl$_3$, majority isomers (46 and 43%)): δ (ppm) 22.54 and 22.57, 22.73, 24.01 and 24.17, 24.69 and 24.77, 26.55 and 27.14, 28.65 and 28.74, 32.20 and 33.78, 32.38 and 32.78, 34.75, 37.71 and 37.79, 39.17 and 39.21, 39.72 and 40.57, 42.07 and 42.20, 74.29 and 74.38.

MS [e/m (%)], 46% isomer: 226 (M+, 0), 155 (38), 137 (20), 115 (100), 111 (14), 97 (54), 95 (15), 81 (13), 71 (12), 69 (25), 57 (11), 55 (32), 43 (26), 41 (19).

MS [e/m (%)], 43% isomer: 226 (M+, 0.4), 156 (10), 155 (100), 137 (24), 95 (12), 83 (13), 81 (15), 69 (18), 57 (13), 55 (16), 43 (17), 41 (15).

MS [e/m (%)], 11% isomer: 226 (M+, 4), 155 (100), 137 (30), 127 (10), 115 (54), 111 (11), 97 (51), 95 (18), 81 (19), 79 (11), 72 (11), 69 (38), 67 (15), 58 (14), 57 (13), 56 (10), 55 (27), 45 (12), 43 (32), 41 (30).

EXAMPLE 15

Perfuming compositions A, B, C and D incorporating one of the derivatives of general formula I which are obtained according to examples 8, 9 and 14.

A patchouli-amber accord A, then the same accord comprising 2-(3,3-dimethylcyclohexyl)butan-2-ol obtained according to example 8 to give accord B, then the same accord comprising 2-(3,3-dimethylcyclohexyl)pent-4-en-2-ol obtained according to example 9 to give accord C, then the same accord comprising 2-(3,3-dimethylcyclohexyl)-5-methylhexan-2-ol obtained according to example 14 to give accord D.

TABLE

Formulations A, B, C and D for masculine eau de toilette

| Ingredients | Accord A | Accord B | Accord C | Accord D |
|---|---|---|---|---|
| BERGAMOT OIL | 0.40 | 0.40 | 0.40 | 0.40 |
| VANILLIN | 3.85 | 3.85 | 3.85 | 3.85 |
| PATCHOULI OIL | 38.45 | 38.45 | 38.45 | 38.45 |
| THYMOL | 0.04 | 0.04 | 0.04 | 0.04 |
| ROCKROSE EXTRACT | 0.38 | 0.38 | 0.38 | 0.38 |
| ETHYLVANILLIN | 0.62 | 0.62 | 0.62 | 0.62 |
| FIXOLIDE ® | 0.77 | 0.77 | 0.77 | 0.77 |
| MUSK KETONE | 1.54 | 1.54 | 1.54 | 1.54 |
| DIPROPYLENE GLYCOL | 53.95 | 50.10 | 50.10 | 50.10 |
| 2-(3,3-dimethylcyclohexyl)butan-2-ol | 0.00 | 3.85 | 0.00 | 0.00 |
| 2-(3,3-dimethylcyclohexyl)pent-4-en-2-ol | 0.00 | 0.00 | 3.85 | 0.00 |
| 2-(3,3-dimethylcyclohexyl)-5-methylhexan-2-ol | 0.00 | 0.00 | 0.00 | 3.85 |

The formulations thus obtained and detailed above are used as perfuming bases: each of these is incorporated at 10% by weight into an alcohol base to prepare a ready-to-use masculine eau de toilette.

The olfactory and comparative evaluation of accords A, B, C and D at 10% by weight in an alcohol base shows that the addition of 2-(3,3-dimethylcyclohexyl)butan-2-ol to the level of 3.85% by weight into accord B accentuates very particularly the musty patchouli facet relative to accord A. The addition of 2-(3,3-dimethylcyclohexyl)pent-4-en-2-ol to the level of 3.85% by weight in accord C also strengthens the patchouli facet as well as the vanilla note relative to accord A. Finally, the addition of 2-(3,3-dimethylcyclohexyl)-5-methylhexan-2-ol to the level of 3.85% by weight in accord D lends a richness to the accord with fruity, smoky, natural notes of dried leaves relative to accord A.

EXAMPLE 16

Perfuming compositions E, F, G and H incorporating one of the derivatives of general formula I which are obtained according to examples 8 and 9.

A fruity-woody cyprus accord E, then the same accord comprising 2-(3,3-dimethylcyclohexyl)butan-2-ol obtained according to example 8 to give accords F et G, then the same accord comprising 2-(3,3-dimethylcyclohexyl)pent-4-en-2-ol is obtained according to example 9 to give accord H.

TABLE

Formulations E, F, G and H for feminine eau de toilette

| Ingredients | Accord E | Accord F | Accord G | Accord H |
|---|---|---|---|---|
| BERGAMOT OIL | 0.77 | 0.77 | 0.77 | 0.77 |
| PATCHOULI OIL | 3.85 | 3.85 | 3.85 | 3.85 |
| ETHYLVANILLIN | 0.77 | 0.77 | 0.77 | 0.77 |
| TEXAS CEDRENE | 0.77 | 0.77 | 0.77 | 0.77 |
| METHYLIONANTHEME SUPER | 0.23 | 0.23 | 0.23 | 0.23 |
| ETHYL LINALOOL | 3.85 | 3.85 | 3.85 | 3.85 |
| FLOROL ® | 4.62 | 4.62 | 4.62 | 4.62 |
| HYDROXYCITRONELLAL | 3.85 | 3.85 | 3.85 | 3.85 |
| GAMMA UNDECALACTONE | 1.54 | 1.54 | 1.54 | 1.54 |
| BETA IONONE | 6.92 | 6.92 | 6.92 | 6.92 |
| METHYL DIHYDROJASMONATE | 21.54 | 21.54 | 21.54 | 21.54 |
| HELIONAL ® | 1.23 | 1.23 | 1.23 | 1.23 |
| EVERNYL ® | 0.15 | 0.15 | 0.15 | 0.15 |
| LYRAL ® | 5.38 | 5.38 | 5.38 | 5.38 |
| CASHMERAN ® | 0.38 | 0.38 | 0.38 | 0.38 |
| DIPROPYLENE GLYCOL | 44.15 | 43.38 | 40.30 | 40.30 |
| 2-(3,3-dimethylcyclohexyl)butan-2-ol | 0.00 | 0.77 | 0.00 | 0.00 |

TABLE-continued

Formulations E, F, G and H for feminine eau de toilette

| Ingredients | Accord E | Accord F | Accord G | Accord H |
|---|---|---|---|---|
| 2-(3,3-dimethylcyclohexyl)butan-2-ol | 0.00 | 0.00 | 3.85 | 0.00 |
| 2-(3,3-dimethylcyclohexyl)pent-4-en-2-ol | 0.00 | 0.00 | 0.00 | 3.85 |

The formulations described above are used as perfuming bases: each of these is incorporated at 12% by weight into a ready-to-use feminine eau de toilette:

The olfactory and comparative evaluation of accords E, F, G and H at 12% by weight in an alcohol base shows that the addition of 2-(3,3-dimethylcyclohexyl)butan-2-ol to the level of 0.77% by weight into accord F is greatly appreciated because it accentuates the smoky fruity facet, relative to accord E. The addition of 2-(3,3-dimethylcyclohexyl)butan-2-ol to the level of 3.85% by weight into accord G very strongly supports the musty, patchouli facet relative to the accord E. Finally, the addition of 2-(3,3-dimethylcyclohexyl)pent-4-en-2-ol 2 to the level of 3.85% by weight in accord H lends a round and warm side relative to accord E.

The invention claimed is:

1. A compound of general formula:

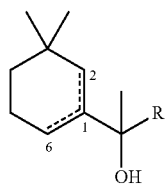

I in which:
the ring with 6 carbon atoms is saturated or has a double bond between carbons C1 and C2 or between carbons C1 and C6,
R is selected from the group consisting of a $C_2$-$C_5$ alkenyl group, a n-propyl, i-propyl, n-butyl, i-butyl, t-butyl or pentyl, 1(or 2)-methylpropyl, 1,2-dimethylpropyl, 1,1-dimethylpropyl, and 1(or 2 or 3)-methylbutyl.

2. The compound according to claim 1, wherein the ring with 6 carbon atoms is saturated.

3. The compound according to claim 1, wherein the ring with 6 carbon atoms has a double bond between carbons C1 and C2 or between carbons C1 and C6.

4. The compound according to claim 1, wherein R is selected from the group consisting of: —$CH_2CH_3$, —$CH_2CH=CH_2$, —$CH_2CH_2CH_3$, —$CH_2CH_2CH_2CH_3$, —$CH_2CH(CH_3)_2$, —$CH(CH_3)CH_2CH_3$ and —$CH_2CH_2CH(CH_3)_2$.

5. The compound according to claim 1, where the compound is selected from the group consisting of:
2-(3,3-dimethylcyclohex-1-enyl)pent-4-en-2-ol
2-(5,5-dimethylcyclohex-1-enyl)pent-4-en-2-ol
2-(3,3-dimethylcyclohex-1-enyl)pentan-2-ol
2-(5,5-dimethylcyclohex-1-enyl)pentan-2-ol
2-(3,3-dimethylcyclohex-1-enyl)hexan-2-ol
2-(5,5-dimethylcyclohex-1-enyl)hexan-2-ol
2-(3,3-dimethylcyclohex-1-enyl)-4-methylpentan-2-ol
2-(5,5-dimethylcyclohex-1-enyl)-4-methylpentan-2-ol
2-(3,3-dimethylcyclohex-1-enyl)-3-methylpentan-2-ol
2-(5,5-dimethylcyclohex-1-enyl)-3-methylpentan-2-ol
2-(3,3-dimethylcyclohex-1-enyl)-5-methylhexan-2-ol
2-(5,5-dimethylcyclohex-1-enyl)-5-methylhexan-2-ol
2-(3,3-dimethylcyclohexyl)pent-4-en-2-ol
2-(3,3-dimethylcyclohexyl)pentan-2-ol
2-(3,3-dimethylcyclohexyl)hexan-2-ol
2-(3,3-dimethylcyclohexyl)-4-methylpentan-2-ol; and
2-(3,3-dimethylcyclohexyl)-5-methylhexan-2-ol.

6. A perfumed composition comprising at least one compound according to claim 1.

7. The composition according to claim 6, wherein the composition is a traditional perfume composition.

8. The composition according to claim 7, wherein the composition is selected from the group consisting of: a perfuming concentrate, an eau de Cologne, an eau de toilette, and a perfume.

9. The composition according to claim 6, wherein the composition is a cosmetic composition.

10. The composition according to claim 9, wherein the composition is selected from the group consisting of: a face and/or body cream, a talcum powder, an oil for the hair or for the body, a shampoo, a hair lotion, bath salts, a bath oil, a shower gel, a bath gel, a soap, an antiperspirant, a deodorant, a lotion, a shaving cream, a shaving soap, a toothpaste, and an ointment.

11. The composition according to claim 6, wherein the composition is a cleaning product.

12. The composition according to claim 11, wherein the composition is selected from the group consisting of: a softener, a detergent, a laundry detergent, an air-freshener, and a room odorizer.

* * * * *